ns Patent [19]

United States Patent [19]
Sykes et al.

[11] 3,980,681
[45] Sept. 14, 1976

[54] PROCESS FOR THE PREPARATION OF 11-β-NITRO-OXYSTEROIDS

[76] Inventors: Peter Job Sykes, Dept. of Chemistry, University of Edinburgh, West Mains Road, Edinburgh 9N; Gordon Hanley Phillipps, 8, Sudbury Hill Close, Wembley, Middlesex; Stuart Bruce Laing, 10, Burwell Ave., Greenford, Middlesex; John Peter Turnbull, 56 Grange Park, Ealing, London W 5, all of England

[22] Filed: Aug. 19, 1974

[21] Appl. No.: 498,470

Related U.S. Application Data

[63] Continuation of Ser. No. 341,104, March 14, 1973, abandoned, which is a continuation of Ser. No. 91,548, Nov. 20, 1970, abandoned.

[30] Foreign Application Priority Data

Nov. 21, 1969 United Kingdom.............. 57084/69
Oct. 27, 1970 United Kingdom.............. 51028/70

[52] U.S. Cl......................... 260/397.45; 260/397.5; 260/397.2
[51] Int. Cl.$^2$......................... C07J 5/00; C07J 1/00
[58] Field of Search .................................................
/Machine Searched Steroids Ceric Ions

[56] References Cited

UNITED STATES PATENTS 3,781,312  12/1973  Hanley et al................... 260/397.45

*Primary Examiner*—Elbert L. Roberts
*Attorney, Agent, or Firm*—Bacon & Thomas

[57] ABSTRACT

Process for preparing 9 α-hydroxy-11 β-nitro-oxysteroids having a aromatic ring A wherein an aromatic A-ring-containing 9, 11-unsubstituted steroid or corresponding 9,11-dehydrosteroid is oxidized with ceric ions in the presence of nitrate ions.

14 Claims, No Drawings

PROCESS FOR THE PREPARATION OF 11β-NITRO-OXYSTEROIDS

This is a continuation of application Ser. No. 341,104, filed Mar. 14, 1973, now abandoned, which is in turn a continuation of application Ser. No. 91,548, filed Nov. 20, 1970, and now abandoned.

This invention relates to a novel method of producing steroid 11β-nitrates.

The presence of a substituent at the 11-position, and in particular an oxygen function, is an important factor determining the physiological activity of many steriods. We have found that it is possible to introduce an 11β-nitrooxy group (—$ONO_2$) and a 9α-hydroxy group into steroids having an aromatic A-ring, which ring may carry one or more oxygen functions e.g. acyloxy or etherified hydroxyl groups. The nitro-oxy group can readily be converted to a hydroxyl group, e.g. by hydrogenation, and subsequent oxidation, e.g. with chromic acid, yields a 9α-hydroxy-11-keto-steroid. The novel reaction described herein thus makes it possible to introduce an 11β-hydroxy or 11-keto group into ring-A aromatic steriods previously unsubstituted at the 9- and 11-positions.

Thus, for example, oestrone acetate may be oxidised to 3-acetoxy-9α, 11β-dihydroxy-oestra-1,3.5(10)-trien-17-one 11β-nitrate, which can be reduced as described hereinafter to yield 3-acetoxy-9α, 11β-dihydroxy-oestra-1,3,5(10)-trien-17-one and the latter can be oxidised with chromic acid to 3-acetoxy-9α-hydroxy-oestra-1,3,5(10)-triene-11,17-dione which is known to exhibit corpus luteum-like hormonal activity. Other 9α-hydroxy-11β-nitro-oxy-oestra-1,3,5(10)-trienes produced according to the invention can be analogously converted.

According to the present invention therefore, we provide a process for the preparation of 9α-hydroxy-11β-nitro-oxy steroids having an aromatic A-ring, in which a 9,11-unsubstituted steriod having an aromatic A-ring which A-ring does not contain an ether group together with a methyl group oxidisable under the reaction conditions, is oxidised by reaction with ceric ions in the presence of nitrate ions.

We have found that the reaction yields predominantly a 9α-hydroxy steroid, but that in most cases some 9β-hydroxy steroid is formed simultaneously, the amount depending in part on the nature of the 17-side chain. The isomers can readily be separated, for example by chromatography.

Laing and Sykes (J. Chem. Soc. 1968(C) 2915–2918) described the oxidation of steroids having an aromatic A-ring containing both a methoxy and a methyl group using ceric salts whereby the ring-A methyl group is oxidised to a formyl group. We have now found that some 9-hydroxy-11β-nitrates can be observed in the reaction products of such reactions and can be isolated as such or as derivatives thereof by conventional methods but the predominant products will be ring-A formylated steroids. On the other hand such a methyl group is not substantially oxidised in the presence of acyloxy groups. In consequence, oxidisable methyl groups will be absent from the A-ring when there is an ether group in the A-ring, and more especially, 1-methyl-3-methoxy and 4-methyl-1-methoxy steroids are not suitable as starting materials. In general it is preferred that the A-ring contains no substituents which are oxidisable under the reaction conditions.

By 'ceric ions' we mean free or complex ions such as are provided by a ceric salt, which should be soluble in wet water-miscible solvents.

Ceric ammonium nitrate is a particularly stable and water soluble ceric salt and is the preferred reagent. Ceric nitrate is also useful; it is most conveniently formed by double decomposition for example by reacting ceric sulphate with barium nitrate in nitric acid. It should be noted that ceric sulphate, which is virtually water-insoluble and in which the ceric ions may be complexed with sulphate anions does not effect the required oxidation reaction. The source of nitrate ions when using a ceric salt other than a nitrate may be nitric acid or any ionisable nitrate soluble in the reaction medium, for example, an alkali metal nitrate or ammonium nitrate.

The reaction is preferably effected in solution in a water-miscible organic solvent advantageously containing a proportion of water. Suitable water-miscible solvent media include, for example ethers such as dioxan, lower fatty acids such as acetic and propionic acids, alcohols such as methanol and t-butanol, ketones such as acetone and methyl ethyl ketone and tertiary amide solvents such as dimethylformamide and dimethylacetamide. The most preferred solvent media are mixtures of dioxan and/or glacial acetic acid and water.

The concentration of ceric salt in the medium is not critical but is preferably in the range 0.2 to 0.5M conveniently about 0.3M.

The reaction appears to use 4 molar equivalents of ceric salt and at least this quantity, therefore, is preferably present initially. When using steroid ring-A ethers however it appears to be advantageous to use a substantial excess of ceric ions, for example about 8 molar equivalents, whereupon the reaction takes place rapidly.

The aromatic A-ring of the steriod starting material may, as indicated above, carry oxygen functions such as acyloxy and/or ether groups. These groups are preferably present in the 3-position, particularly since the resulting products may then be more directly converted into useful physiologically active end products.

The acyloxy groups may, for example, be derived from a substituted or unsubstituted carboxylic or hydrocarbonsulphonic acid preferably having up to 20 carbon atoms; or from sulphuric acid, nitric acid or phosphoric acid; for example an aromatic carboxylic acid such as benzoic, o-nitrobenzoic or toluic acid, an araliphatic carboxylic acid such as phenylacetic or phenylpropionic acid, an aliphatic carboxylic acid such as acetic, propionic or trifluoroacetic acid, an aliphatic sulphonic acid such as methanesulphonic acid or an aromatic sulphonic acid such as toluene p-sulphonic or benzenesulphonic acid.

The ether groups preferably have up to 20 carbon atoms and may, for example, be substituted or unsubstituted aliphatic, araliphatic, cycloaliphatic, aromatic or heterocyclic ether groups. Aliphatic ether groups include alkoxy groups, preferably having 1–6 carbon atoms, for example methoxy, ethoxy, propoxy, butoxy or hexyloxy groups. Cycloaliphatic ether groups include cycloalkoxy groups, preferably having 5–7 carbon atoms, for example cyclopentyloxy or cyclohexyloxy groups. Araliphatic groups preferably have 1–6 carbon atoms in the aliphatic portion and preferably include monocyclic rings, examples being benzyloxy, phenethoxy and nitrobenzyloxy groups. Aromatic ether groups are preferably monocyclic and include, for example, phenoxy, tolyloxy and p-nitrophenoxy groups.

The C-ring of the steroid is preferably unsubstituted. The B-ring is preferably saturated and it is also preferred that there is no substituent at the 6-position. The 1- or 4-positions of the A-ring may, however, carry substituents such as alkyl groups, e.g. methyl groups and the 16-position may carry a halogen atom, an alkyl group, e.g. a methyl group, or a methylene group. The 13-position may carry an alkyl group, for example a methyl or ethyl group. The 17-position may carry, for example, a keto group, or a hydrogen atom or a hydroxy or acyloxy group which may be present together with a hydrogen atom or a saturated or unsaturated hydrocarbon group such as an alkyl group which may carry substituents such as keto, protected keto, hydroxy or acyloxy groups. Where alkyl and/or acyloxy groups are present these preferably contain 1–6 carbon atoms.

The starting steroid may be in the 9α-series or the 9β-series. By the term '9,11-unsubstituted steroid] we mean a steroid possessing only hydrogen atoms at positions 9 and 11.

The reaction is capable of giving high yields of the desired product and, for example, oestrone acetate is oxidised by the use of 4 molar equivalents of ceric ammonium nitrate to 3-acetoxy-9α,11β-dihydroxy-oestra-1,3,5(10)-trien-17-one 11β-nitrate in 70% yield.

While we do not wish to be bound by theoretical considerations, it is believed that the reaction proceeds by removal of a hydrogen radical and an electron from the 9-position to leave a positive charge which effects elimination of an 11-proton to generate a 9,11-double bond. It is believed that this bond then forms an α-face complex with a ceric ion which allows nucleophilic attack at the 11β-position by the most reactive nucleophile present, usually the nitrate anion, to give a free radical (single electron) at the 9-position which reacts with a ceric ion to yield a positive charge which then reacts with a small nucleophile, for example a water molecule. It will be seen, therefore, that to obtain the 11β-nitrate, it is necessary for nitrate ions to be present and it seems likely that water is necessary for the hydroxylation at the 9α-position.

It can be shown that the same product is obtained using the proposed intermediate 9,11-dehydro compound as starting material and this both confirms part of the above theoretical explanation of the reaction and constitutes a variation of the process according to the invention. A further variation on this procedure is to use a 9-hydroxy-ring-A aromatic steriod starting material which under the conditions of the reaction undergoes dehydration to give the 9,11-dehydro steriod followed by oxidation to give the 9-hydroxy-11β-nitro-oxy steriod. Thus, for example 3-acetoxy-9α-hydroxyoestra-1,3,5(10)-trien-17-one yields the corresponding 11β-nitrate.

The reduction of the 9α-hydroxy-11β-nitro-oxy-steroids according to the invention, as described above, can, for example, be effected by catalytic hydrogenation, e.g. in the presence of a noble metal catalyst such as palladium, conveniently on a charcoal support. The reaction proceeds more rapidly in the presence of a base, for example an amine such as triethylamine. Other reducing agents include zinc e.g. in acetic acid or aqueous ethanol, and palladium/hydrazine.

The 9α,11β-dihydroxy steroid can be oxidised with a reagent serving to oxidise a secondary alcohol grouping to a keto group, for example chromic acid, advantageously in acetone (Jones' reagent) preferably at a relatively low temperature e.g. −10° to +10°C.

The 9α-hydroxy-11β-nitro-oxy steroid 3-esters and 3-ethers prepared by the process according to the invention are also of use in the preparation of 3-hydroxy-9α-H-11α-hydroxy ring A-aromatic steroids: reduction of a 3-hydroxy-9α-hydroxy-11β-nitro-oxy-ring A-aromatic steroid (obtainable from the corresponding steroid 3-ester or 3-ether), or of a 3-acyloxy-9α-hydroxy-11β-nitro-oxy-ring A-aromatic steroid itself, with a borohydride reducing agent leads to the formation of the said 9α-H-11α-hydroxy product, of particular interest as intermediates in the preparation of the corresponding 11β-halogeno steroids as described in our British Pat. Nos. 1159434 and 1202521. The reaction is preferably effected in a polar solvent at ambient or elevated temperature.

The following examples are given by way of illustration only. All temperatures are in °C, melting points were determined in open capillaries and are corrected. Optical rotations were measured for chloroform solutions unless otherwise stated. Infra red spectra were measured for bromoform solutions. Plates for thin-layer chromatography were coated with Merck Kieselgel $PF_{254+366}$ and were visualised by spraying with 2N-sulphuric acid and baking at ca. 150°. Preparative layer chromatography was effected on similar plates developed with chloroform or chloroform-isopropanol mixtures.

EXAMPLE 1

3,17α-Diacetoxy-9β,11β-dihydroxy-19-nor-9β-pregna-1,3,5(10)-trien-20-one 11β-nitrate To a stirred solution of 3,17α-diacetoxy-19-norpregna-1,3,5(10),9(11)-tetraen-20-one (800 mg., 2 mmole) in dioxan (20 ml.) at room temperature was added M-aqueous ceric ammonium nitrate (4.5 ml., 1.12 equiv.). After 2 min., the solution was poured into water (100 ml.) and the product was extracted into ethyl acetate (2 × 50 ml.). The extracts were washed with water (2 × 50 ml.) and the solvent evaporated in vacuo to give a pale yellow froth (1.1 g.).

Repeated preparative thin-layer chromatography of the product yielded the title compound (72 mg., 7.5%) as a white froth, $v_{max}$. 3590, 1750, 1730, 1720, 1640 and 1360 cm.$^{-1}$.

EXAMPLE 2

3-Acetoxy-9β-oestra-1,3,5(10)-trien-17-one

3-Hydroxy-9β-oestra-1,3,5(10)-trien-17-one (370 mg., 1.4 mmole) was treated with acetic anhydride (3 ml.) in pyridine (3 ml.) at steam-bath temperature for 45 min. The cooled solution was poured into water (50 ml.), and extracted with ether (50 ml.). The ether extract was washed with 2N-sulphuric acid (25 ml.), then water (2 × 25 ml.) and the solvent evaporated in vacuo to give the title compound as a chromatographically pure oil (390 mg., 90%), $v_{max}$. 1758, 1735 and 1200 cm.$^{-1}$.

EXAMPLE 3

3-Acetoxy-9α,11β-dihydroxy-oestra-1,3,5(10)-trien-17-one 11β-nitrate.

To a stirred solution of 3-acetoxy-9β-oestra-1,3,5(10)-trien-17-one (325 mg., 1.04 mmole) in acetic acid (6 ml.) at room temperature was added M-aqueous ceric ammonium nitrate (4.5 ml., 1.08 equiv,). After 15 min., the solution was poured into water (50 ml.) and the product extracted into ether (50 ml.). The extract was washed with water (2 × 25 ml.), then 10% aqueous potassium hydrogen carbonate (25 ml.) and the solvent was evaporated in vacuo. Preparative thin-layer chromatography of the residue (370 mg.) and crystallisation from cyclonexane-ether gave the title compound (170 mg., 44%), m.p. 182°–184° (dec.).

EXAMPLE 4

3,17β-Diacetoxy-9α,11β-dihydroxy-oestra-1,3,5(10)-triene 11β-nitrate and
3,17β-diacetoxy-9β,11β-dihydroxy-9β-oestra-1,3,5(10)-triene 11β-nitrate.

To a stirred solution of 3,17β-diacetoxy-oestra-1,3,5(10)-triene (1.08 g., 3 mmoles) in acetic acid (22 ml.) at room temperature was added M-aqueous ceric ammonium nitrate (15 ml., 1.25 equiv.). After 30 min. the solution was poured into water (100 ml.) and extracted with ether. The extract was washed with water (2 × 50 ml.) then with 10% potassium hydrogen carbonate (25 ml.) and the solvent was evaporated in vacuo to give a pale yellow froth (1.35 g.). Thin-layer chromatography of the product gave the crude title compounds as froths (766 mg., 60% and 322 mg., 25% respectively).

Recrystallisation of the major product from cyclohexane-methylene chloride gave pure 3,17β-diacetoxy-9α,11β-dihydroxy-oestra-1,3,5(10)-triene 11β-nitrate as prisms (592mg., 46%), m.p. 177°–178°, $[\alpha]_D + 21°$ (c, 0.50).

Rechromatography of the minor product gave pure 3,17β-diacetoxy-9β,11β-dihydroxy-9β-oestra-1,3,5(10)-triene 11β-nitrate as a colourless froth (227 mg., 17%), $v_{max.}$ 3620, 1750, 1730, 1635, 1370, 1250 and 1205 cm.$^{-1}$.

EXAMPLE 5

3,20β-Diacetoxy-19-norpregna-1,3,5,(10)-triene.

3,20β-Dihydroxy-19-norpregna-1,3,5(10)-triene (4.4 g., 14.6 mmole) was heated on the steam-bath for 1 hour with acetic anhydride (22 ml.) in pyridine (22 ml.). The cooled solution was gradually diluted with water (150 ml.) to give the crude title compound (5.5 g., 95%) as fine yellow needles, m.p. 120°–126°. After passage through a short Florisil column in methylene chloride, the product was crystallized from cyclohexane to give the pure title compound as clusters of needles (3.93 g., 70%), m.p. 132°–133°, $[\alpha]_D^{24} + 67.5°$ (c, 0.80).

EXAMPLE 6

3,20β-Diacetoxy-9α,11β-dihydroxy-19-norpregna-1,3,5(10)-triene 11β-nitrate and
3,20β-diacetoxy-9β,11β-dihydroxy-19-nor-9β-pregna-1,3,5,(10)-triene 11β-nitrate.

Following the method in Example 4, but using three volumes of acetic acid, 3,20β-diacetoxy-19-norpregna-1,3,5(10)-triene (384 mg., 1 mmole) afforded the title compounds as froths (130 mg., 28% and 97 mg., 21% respectively). Crystallisation of the former compound from cyclohexane - ether gave prisms (102 mg., 22%), m.p. 174.5°–175.5°. The latter compound, which did not crystallise, had $v_{max.}$ 3610, 1750, 1720, 1640, 1280, 1250 and 1210 cm.$^{-1}$.

EXAMPLE 7

9α,11β-Dihydroxy3-methanesulphonyl-oxy-oestra-1,3,5(10)-trien-17-one 11β-nitrate.

A stirred solution of 3-methanesulphonyloxy-oestra-1,3,5(10)-trien-17-one (349 mg., 1 mmole) in acetic acid (10ml.) at room temperature was treated with M-aqueous ceric ammonium nitrate (5 ml., 1.25 equiv.). After 3.5 hr. the solution was poured into water (50 ml.) and the product extracted into ether (50 ml.). The extract was washed with water (2 × 50 ml.) then 10% potassium hydrogen carbonate solution (25 ml.) and the solvent was evaporated in vacuo. Preparative thin-layer chromatography of the residue (375 mg.) and crystallisation from cyclohexane — acetone gave the title compound as blades (132 mg., 31%), m.p. 189°–191° (dec.).

EXAMPLE 8

3-Toluene-p-sulphonyloxy-oestra-1,3,5(10)-trien-17-one.

Oestrone (2 g., 7.4 mmole) in pyridine (10 ml.) was treated at room temperature for 3 days with toluene-p-sulphonyl chloride (2 g., 1.4 equiv.). The stirred mixture was slowly diluted with water (40 ml.). The precipitated oil slowly crystallized on agitation. Recrystallisation from methanol—methylene chloride gave the title compound plates (2.65 g., 85%), m.p. 143°–145°, $[\alpha]_D$ + 105°. (c, 1.00).

EXAMPLE 9

9α,11β-Dihydroxy-3-toluene-p-sulphonyloxy-oestra-1,3,5(10)-trien-17-one 11β-nitrate.

To a stirred solution of 3-toluene-p-sulphonyloxy-oestra-1,3,5(10)-trien-17-one (425 mg., 1 mmole) in acetic acid (10 ml.) at room temperature was added M-aqueous ceric ammonium nitrate (5 ml., 1.25 equiv.). After 7 hr., the solution was poured into water (50 ml.) and the product was extracted into ether (50 ml.). The extract was washed with water (2 × 50 ml.) then with 10% potassium hydrogen carbonate solution, and the solvent was evaporated in vacuo. Thin-layer chromatography of the residue, and crystallisation from cyclohexane — methylene chloride afforded the title compound as prisms (135 mg., 27%), m.p. 193°–194° (dec.) $[\alpha]_D$ + 110° (c, (1.00).

EXAMPLE 10

3-Phenylacetoxy-oestra-1,3,5(10)-trien-17-one.

Oestrone (2 g.) in pyridine (10 ml.) was treated for three days at room temperature with phenylacetyl chloride (3 ml.). The mixture was diluted with water (50 ml.) and the product extracted with ether (50 ml.) containing a little chloroform. The extract was washed with water (50 ml.) then 2N-sulphuric acid (25 ml.) then water again (50 ml.) and the solvent was evaporated in vacuo. Filtration of the residue in methylene chloride through a short Florisil column and crystallisation from light petroleum (b.p. 40°/60°)-ether gave the title compound in two crops (total 1.54 g., 54%), m.p. 114°–116°.

EXAMPLE 11

9α,11β-Dihydroxy-3-phenylacetoxy-oestra-1,3,5(10)-trien-17-one 11β-nitrate.

To a stirred solution of 3-phenylacetoxy-oestra-1,3,5(10)-trien-17-one (388 mg., 1 mmole) in acetic acid (10 ml.) at room temperature was added M-aqueous ceric ammonium nitrate (5 ml., 1.25 equiv.). After 30 min. the solution was poured into water (50 ml.) and the product extracted into ether (2 × 50 ml.). The combined extracts were washed with water (2 × 50 ml.) then 10% potassium hydrogen carbonate (2 × 20 ml.) then water (50 ml.) and the solvent was evaporated in vacuo. Thinlayer chromatography of the residue and crystallisation from light petroleum (b.p. 40°–60°)-ether afforded the title compound as small prisms (110 mg., 24%), m.p. 131°–133°, $[\alpha]_D + 87.5°$ (c, 1.00).

EXAMPLE 12

3-Benzoyloxy-9α,11β-dihydroxy-oestra-1,3,5(10)-trien-17-one 11β-nitrate.

To a stirred solution of 3-benzoyloxy-oestra-1,3,5(10)-trien-17-one (375 mg., 1 mmole) in acetic acid (10 ml.) at room temperature was added M-aqueous ceric ammonium nitrate (5 ml., 1.25 equiv.). After 18 hr. the solution was poured into water and the product extracted into ether (2 × 50 ml.). The extracts were washed with water (50 ml.), then 10% potassium hydrogen carbonate (50 ml.) then water (50 ml.) and the solvent was evaporated in vacuo. Thin-layer chromatography of the residue and crystallisation from ether gave the title compound as prisms (135 mg., 30%), m.p. 181°–182°, $[\alpha]_D + 90°$ (c, 1.00).

EXAMPLE 13

3-Acetoxy-19-norcholesta-1,3,5(10)-triene.

3-Hydroxy-19-norcholesta-1,3,5(10)-triene (1.0 g., 2.7 mmole) in pyridine (3 ml.) was treated with acetic anhydride (3 ml.) at room temperture for 16 hr. Slow dilution of the solution at 0° with water (20 ml.) gave a precipitate of fine pale yellow needles. Recrystallisation from methanol - ether afforded the title compound as colourless plates (900 mg., 81%), m.p. 76.5°–77.5°.

EXAMPLE 14

3-Acetoxy-9α,11β-dihydroxy-19-norcholesta-1,3,5(10)-triene 11β-nitrate and
3-acetoxy-9β,11β-dihydroxy-19-nor-9β-cholesta-1,3,5(10)-triene 11β-nitrate.

Following the method of Example 4, but using ceric ammonium nitrate (2 g.) in 66% acetic acid (3 ml.) in place of M-aqueous ceric ammonium nitrate, 3-acetoxy-19-norcholesta-1,3,5(10)-triene (410 mg., 1 mmole) afforded the crude title compounds as froths (160 mg., 33%) and (150 mg., 30%) respectively. Recrystallisation of the former compound from cyclohexane gave prisms (105 mg., 22%), m.p. 171°–172° (dec.) and crystallisation of the latter compound, also from cyclohexane gave prisms (78 mg., 16%), m.p. 94°–95°.

EXAMPLE 15

3-Acetoxy-17β-benzoyloxy-oestra-1,3,5(10)-triene

3-Acetoxy-oestra-1,3,5(10)-trien-17β-ol (500 mg., 1.6 mmole) in pyridine (2 ml.) was treated with benzoyl chloride (1.0 ml.) at room temperature for 16 hr. The stirred mixture was then slowly diluted with water (10 ml.), followed by methanol (5 ml.). The crystalline precipitate was filtered off, washed with water and dried to give the title compound (665 mg., 100%), m.p. 148.5°–150.5°.

EXAMPLE 16

3-Acetoxy-17β-benzoyloxy-9β,11β-dihydroxy-oestra-1,3,5 (10)-triene 11β-nitrate and
3-acetoxy-17β-benzoyloxy-9β,11β-dihydroxy-9β-oestra-1,3,5(10)-triene 11β-nitrate.

Following the method of Example 14, 3-acetoxy-17β-benzoyloxy-oestra-1,3,5(10)-triene (419 mg., 1 mmole) afforded the crude title compounds as froths (215 mg., 43%) and (90 mg., 18%) respectively. The former compound, which failed to crystallise, had $[\alpha]_D + 43°$ (c, 0.50), $v_{max.}$ 3640, 1750, 1710, 1630, 1275 and 1210 cm.$^{-1}$. The latter compound crystallised from cyclohexane -ether as prisms (50 mg., 10%), m.p. 150°–152° (dec.).

EXAMPLE 17

3-Acetoxy-17β-methanesulphonyloxy-oestra-1,3,5(10)-triene.

3-Acetoxy-oestra-1,3,5(10)-trien-17β-ol (500 mg., 1.6 mmole) in pyridine (2 ml.) was treated at room temperature for 16 hr. with methanesulphonyl chloride (1 ml.). The solution was diluted slowly with water (25 ml.) then the product was extracted into ether (50 ml.). The extract was washed with 2N-sulphuric acid (25 ml.) then water (50 ml.) and the solvent was evaporated in vacuo. Crystallisation of the residue from slightly aqueous methanol gave the title compound in two crops (total 519 mg., 93%), m.p. 120°–122°.

EXAMPLE 18

3-Acetoxy-9β,11β-dihydroxy-17β-methanesulphonyloxy-oestra-1,3,5(10)-triene 11β-nitrate and
3-acetoxy-9β,11β-dihydroxy-17β-methanesulphonyloxy-9β-oestra-1,3,5(10)-triene 11β-nitrate.

Following the method of Example 14, 3-acetoxy-17β-methansulphonyloxy-oestra-1,3,5(10)-triene (365 mg., 0.9 mmole) afforded the crude title compounds as froths (220 mg., 50% and 35 mg., 20% respectively). The former compound crystallised from methanol (130 mg., 30%), m.p. 145°–146°. The latter compound, which did not crystallise had $[\alpha]_D + 4°$ (c, 0.50).

EXAMPLE 19

9α,11β-Dihydroxy-3-methoxy-oestra-1,3,5(10)-trien-17-one 11β-nitrate.

To a stirred solution of 3-methoxy-oestra-1,3,5(10)-trien-17-one (285 mg., 1 mmole) in dioxan (10 ml.) at room temperature was added ceric ammonium nitrate (4.4 g., 8 mmole) in 66% acetic acid (8 ml.). After 20 min., the solution was poured into water (50 ml.) and the product extracted into ethyl acetate (50 ml.). The extract was washed with water (2 × 25 ml.) then 10% potassium hydrogen carbonate (25 ml.) then water (25 ml.) and the solvent was evaporated in vacuo. Thinlayer chromatography of the residue and crystallisation from aqueous methanol gave the title compound (60 mg., 17%), m.p. 168°–169° (dec.).

EXAMPLE 20

9β, 11β-Dihydroxy-3-methoxy-oestra-1,3,5(10)-trien-17-one nitrate

Appropriate chromatographic fractions from the reaction described in Example 19 and from three similar reactions were combined and rechromatographed to give the title compound as a froth (125 mg., 8.5%), $v_{max}$. 3680, 1730, 1630, 1275, 1250 and 1030 cm.$^{-1}$.

EXAMPLE 21

3-Acetoxy-9α,11β-dihydroxy-oestra-1,3,5(10)-trien-17-one 11β-nitrate.

3-Acetoxyoestra-1,3,5(10)-trien-17-one (5.00 g.) in acetic acid (50 ml) was treated over 20 min. with a solution of ceric ammonium nitrate (29.8 g.) in acetic acid (40 ml.) and water (10 ml). The solution was stirred for a further 20 minutes, then poured into water (300 ml) and the precipitated steroid extracted into ethyl acetate. The solution was washed with sodium carbonate solution, then water, dried and the solvent evaporated to give a pale yellow oil. Crystallisation from ethanol gave the title compound (2.31 g). Filtration of the mother liquors, in benzene, through magnesium silicate gave, after crystallisation, further product (1.98 g, 69% total yield), m.p. 187°–188°(dec.); $[\alpha]_D$ + 95°, (c. 0.79). $v_{max}$ (CHBr$_3$) 3570 (hydroxyl), 1730 (17-ketone), 1745 and 1210 (3-acetate), and 1630 and 1270 cm$^{-1}$ (nitrate ester); $\lambda_{max}$ 266 nm ($\epsilon$ 550).

EXAMPLE 22

3-Acetoxy-9α, 11β-dihydroxy-oestra-1,3,5(10)-trien-17-one 11β-nitrate

3-Acetoxy-oestra-1,3,5(10)-trien-17-one (313 mg; 1 mmole) in acetic acid (5 ml.) was treated with stirring at room temperature with M aqueous ceric ammonium nitrate (4.5 ml; 1.12 equiv.) in one lot. Slow aqueous dilution of the stirred reaction mixture after 5 min. afforded the crude title compound (221 mg; 57%) m.p. 175°–178° (dec.).

EXAMPLE 23

3-Acetoxy-9α, 11β-dihydroxy-oestra-1,3,5(10)-trien-17-one 11β-nitrate

3-Acetoxy-oestra-1,3,5(10)-trien-17-one (313 mg; 1 mmole) in propionic acid (5 ml.) was treated with stirring at room temperature with M aqueous ceric ammonium nitrate (4.5 ml; 1.12 equiv.) in one lot. Slow aqueous dilution of the stirred reaction mixture after 5 min. afforded the crude title compound (170 mg; 44%) m.p. 177°–179° (dec.).

EXAMPLE 24.

3-Acetoxy-9α, 11β-dihydroxy-oestra-1,3,5(10)-trien-17-one 11β-nitrate

3-Acetoxy-oestra-1,3,5(10)-trien-17-one (313 mg; 1 mmole) in dioxan (5 ml.) was treated with stirring at room temperature with M aqueous ceric ammonium nitrate (4.5 ml; 1.12 equiv.) in one lot. After 45 min. the solution had faded to pale yellow, and thin-layer chromatography (using light petroleum (b.p. 40°–60°): acetone (3:1); 2 runs) indicated formation of the title compound ($R_f$~0.45, unseparated on admixture with authentic material) in ca. 50% amount.

EXAMPLE 25

3-Acetoxy-9α,11β-dihydroxy-oestra-1,3,5(10)-trien-17-one 11β-nitrate

3-Acetoxy-oestra-1,3,5(10)-trien-17-one (313 mg; 1 mmole) in acetone (5 ml.) was treated with stirring at room temperature with M aqueous ceric ammonium nitrate (4.5 ml.; 1.12 equiv.) in one lot. After 20 min., the solution had faded to pale yellow and thin-layer chromatography (using light petroleum (b.p. 40°–60°)-/acetone (3;1); 2 runs) indicated formation of the title compound ($R_f$~0.45, unseparated on admixture with authentic material) in ca. 30% amount.

EXAMPLE 26

3-Acetoxy-9α,11β-dihydroxy-oestra-1,3,5(10)-trien-17-one 11β-nitrate

3-Acetoxy-oestra-1,3,5(10), 9(11)-tetraen-17-one (2.6 g; 8.4 mmole) in acetic acid (30 ml.) was treated with ceric ammonium nitrate (12 g.) in acetic acid (15 ml.) and water (5 ml.). After stirring at room temperature for 20 min., water (100 ml.) was added. The precipitated steroid was washed with water, dried and recrystallised from ethanol to give the title compound (0.980g; 31%) m.p. 187°–188° (dec.) $[\alpha]_D$ + 101.3° (c.0.98).

EXAMPLE 27

3-Acetoxy-9α,11β-dihydroxy-oestra-1,3,5(10)-trien-17-one

3-Acetoxy-9α,11β-dihydroxy-oestra-1,3,5(10)-trien-17-one 11β-nitrate (2.7 g) in ethyl acetate (100 ml) with 5% palladium-on-charcoal catalyst (1.3 g.) was hydrogenated at atmospheric pressure and room temperature until hydrogen uptake ceased. The catalyst was filtered off and the solvent was evaporated to give a white froth which was crystallized from methanol to give the title compound (2.07 g, 86%), m.p. 199°–201°C, $[\alpha]_D$ + 186° (c.0.97).

EXAMPLE 28

3-Acetoxy-9α,11β-dihydroxy-oestra-1,3,5(10)-trien-17-one

3-Acetoxy-9α,11β-dihydroxy-oestra-1,3,5(10)-trien-17-one 11β-nitrate (51 mg.) in acetic acid (10 ml) was stirred at room temperature with zinc powder (200 mg.) for 1.2 hr. The reaction mixture was filtered, the acid phase diluted with water and the precipitated steroid extracted into ethyl acetate. The solution was washed with sodium carbonate solution and water, dried, and the solvent was evaporated. Crystallisation from methanol gave the title compound (28 mg, 63%), m.p. 198.5°–200°.

EXAMPLE 29

3-Acetoxy-9α-hydroxy-oestra-1,3,5(10)-triene-11,17-dione

3-Acetoxy-9α,11β-dihydroxy-oestra-1,3,5(10)-trien-17-one (690 mg.) in acetone (30 ml) at 5° was treated dropwise with stirring with 8N chromic acid (1.0 ml). The solution was stirred for 5 mins. then methanol (1 ml), and water (30 ml) were added. The organic solvents were distilled off in vacuo and the steroid extracted into ethyl acetate. The organic solution was washed with dilute hydrochloric acid, then water, dried and the solvent was evaporated. The resulting gum was crystallised from methanol to give the title compound (247 mg, 36%), m.p. 247°–8°, $[\alpha]_D$ + 297° (c. 1.0 in dioxan).

EXAMPLE 30

3-Propionyloxy-oestra-1,3,5(10)-trien-17-one

3-Hydroxy-oestra-1,3,5(10)-trien-17-one (2 g) in pyridine (20 ml.) and propionic anhydride (20 ml) was allowed to stand at room temperature for 1 hour. The solution was poured into ice-water (250 ml) and the precipitated steroid was extracted into ethyl acetate. The organic solution was washed with sodium carbonate solution, then water, dried and the solvent was evaporated. Crystallisation from ethyl acetate gave the title compound (2.10 g, 88%). m.p. 134°–6°, $[\alpha]_D$ + 136° (c. 1.03).

EXAMPLE 31

9α,11β-Dihydroxy-3-propionyloxy-oestra-1,3,5(10)-trien-17-one 11β-nitrate

3-Propionyloxy-oestra-1,3,5(10)-trien-17-one (326 mg; 1 mmole) in acetic acid (3.5 ml.) was treated at room temperature with ceric ammonium nitrate (2.3 g; 1.05 equiv.) in water (3.5 ml) and acetic acid (5 ml.). After 15 min, the mixture was poured into water, extracted with ether (2×50 ml.) and the extracts washed with water (2×50 ml), 10% potassium-hydrogen carbonate (50 ml.) and evaporated. Crystallisation of the residue from cyclohexane-ether gave the title compound (166 mg; 42%) m.p. 179°–182° (dec). A recrystallised sample (methanol-methylene chloride) had m.p. 187°–188° (dec.), $[\alpha]_D$ + 99° (c. 0.80)

EXAMPLE 32

9α,11β-Dihydroxy-3-propionyloxy-oestra-1,3,5(10)-trien-17-one 11β-nitrate

3-Propionyloxy-oestra-1,3,5(10)-trien-17-one (376 mg; 1 mmole) in acetic acid (5 ml) was treated at room temperature with M aqueous ceric ammonium nitrate (4.5 ml; 1.12 equiv) in one lot. Slow aqueous dilution of the reaction mixture after 5 min. gave the title compound (215 mg; 53%) m.p. 180°–182° (dec.)

EXAMPLE 33

3,17α-Diacetoxy-19-norpregna-1,3,5(10)-trien-20-one and 3,17α-diacetoxy-19-nor-9β-pregna-1,3,5(10)-trien-20-one 3,17α-biacetoxy-19-norpregna-1,3,5(10),9(11)-tetraen-20-one 16.0 g; 15.2 mmole) suspended in ethyl acetate (300 ml.) was hydrogenated at room temperature and atmospheric pressure over 10% palladium-on-charcoal (600 mg.). When 386 ml. (1.08 equiv) had been absorbed in 100 min, the reaction was stopped, the catalyst was filtered off and the filtrate was evaporated until crsytallisation commenced, giving 3,17α-diacetoxy-19-norpregna-1,3,5(10)-trien-20-one (1.8 g, 30%) m.p. 191°–194° containing ca. 5% of the 9β isomer.

The mother liquor was evaporated to dryness and crystallised from slightly aqueous methanol to give a ca. 2:1 mixture of 3,17α-diacetoxy-19-nor-9β-pregna-1,3,5(10)-trien-20-one and its 9α-isomer (3.1 g; 61%) m.p. 142°–149°. Preparative thin-layer chromatography of 220 mg of this material gave the pure 9β-compound (131 mg; 60%), m.p. 158°–159°, $[\alpha]_D$–32° (c. 1.04).

EXAMPLE 34

3,17α-Diacetoxy-9α,11β-dihydroxy-19-norpregna-1,3,5(10)-trien-20-one 11β-nitrate A stirred suspension of 3,17α-diacetoxy-19-norpregna-1,3,5(10),9(11)-tetraen-20-one (400 mg; 1 mmole) in glacial acetic acid (5ml.) and dioxan (5 ml.) was treated dropwise at room temperature with M aqueous ceric ammonium nitrate (2.3 ml; 1.15 equiv). After disappearance of the transient red colour (less than 1 min.) the solution was poured into water (50 ml.) extracted with ethyl acetate (2×50 ml.) and the extracts washed twice with water and evaporated to give a yellow froth (490 mg.).

Preparative thin-layer chromatography of the froth yielded pure 3,17α-diacetoxy-9α,11β-dihydroxy-19-norpregna-1,3,5(10)-trien-20-one 11β-nitrate (280 mg; 60%) which crystallised from cyclohexane/ether as a white microcrystalline powder (155 mg) m.p. 146°–153° (dec).

Similar reactions using dioxan/acetic acid (2:1), dioxan/acetic acid (3:1) or pure dioxan (each 10 ml.) in place of dioxan/acetic acid (1:1) as described above gave yields of 300 mg. 295 mg. and 295 mg. respectively of chromatographically pure hydroxy-nitrate (ca. 65% each).

EXAMPLE 35

3,17α-Diacetoxy-9α,11β-dihydroxy-19-norpregna-1,3,5(10)-trien-20-one 11β-nitrate A stirred solution of 3,17α-diacetoxy-19-norpregna-1,3,5(10)-trien-20-one (200 mg; 0.5 mmole) in glacial acetic acid (5 ml.) was treated at room temperature with M aqueous ceric ammonium nitrate (2.1 ml; 1.05 equiv.). After the initial red colour had faded to pale yellow (20 min.) the solution was diluted with water (50 ml.) and extracted with ether (2×50 ml.). The combined extracts were washed with water (50 ml.), 10% potassium hydrogen carbonate (50 ml.), then water again (50 ml.), and evaporated under reduced pressure to give a yellow froth (223 mg.) shown by thin-layer chromatography (using chloroform; 3 runs) to contain ca. 65% of the title compound $R_f$~0.30).

EXAMPLE 36

3,17α-Diacetoxy-9α,11β-dihydroxy-19-norpregna-1,3,5(10)-trien-20-one 11β-nitrate A 2:1 mixture of 3,17α-diacetoxy-19-nor-9β-pregna-1,3,5(10)-trien-20-one and 3,17α-diacetoxy-19-nor-pregna-1,3,5(10)-trien-20-one (described in Example 33) (200 mg; 0.5 mmole) in acetic acid (5 ml) was treated with M aqueous ceric ammonium nitrate (2.1 ml, 1.05 equiv.) at room temperature. After 20 min, the solution was poured into water (50 ml.) and extracted with ether (2×50 ml.). The combined extracts were washed with water (50 ml.), 10% potassium hydrogen carbonate (50 ml.), then water again (50 ml), and evaporated under reduced pressure to give a yellow froth (228 mg.), shown by thin-layer chromatography (chloroform; 3 runs) to contain ca. 65% of the title compound ($R_f$~0.30).

This product and that from Example 35 were combined for preparative thin-layer chromatography which afforded a colourless froth (260 mg; 57%). Crystallisation of this froth from aqueous methanol gave the title compound as a white micro-crystalline powder (105 mg; 22%), m.p. 150°–155° (dec.), $[\alpha]_D$ 30 18° (c. 0.60).

EXAMPLE 37

3,17α-Diacetoxy-9α,11β-dihydroxy-19-norpregna-1,3,5(10)-trien-20-one

A 1:1 mixture of 3,17α-diacetoxy-19-norpregna-1,3,5(10)-trien-20-one and its 9α-isomer (3.53 g : 9 mmole) was dissolved in glacial acetic acid (90 ml.) and M aqueous ceric ammonium nitrate (36 ml.; 1.00 equiv) was added in one lot to the stirred solution at room temperature. After 20 min. the reaction mixture was poured into water (500 ml) extracted with ether (2×200 ml.) and the extracts were washed with water (3×200 ml), then 10% potassium hydrogen carbonate (2×100 ml.) and evaporated under reduced pressure to give a yellow froth (4.2 g).

The froth, in ethyl acetate (200 ml.) was then hydrogenated at room temperature and atmospheric pressure over 10% palladium-on-charcoal (1.5 g.) until uptake became slow (536 ml in 2 hr.). The catalyst was then filtered off and after removal of the solvent under reduced pressure the product was chromatographed over magnesium silicate using methylene chloride-acetone mixtures. The fractions eluted with 5% and 10% acetone were combined (1.3 g; 35%) and crystallised from ethyl acetate-cyclohexane to give the title compound (685 mg; 18%). A recrystallised sample had m.p. 211°–213°, $[\alpha]_D$ + 97.5° (c. 1.0).

EXAMPLE 38

3,17α-Diacetoxy-9α,11β-dihydroxy-1-methyl-19-norpregna-1,3,5(10)-trien-20-one 11β-nitrate 3,17α-Diacetoxy-1-methyl-19-norpregna-1,3,5(10),9(11)-tetraen-20-one (380 mg) in acetic acid (10 ml.) was treated with stirring with a solution of ceric ammonium nitrate (2.0 g) in acetic acid (8 ml.) and water (2 ml.). The initially red colour disappeared after 10 min., when t.l.c. showed that no starting material remained. The mixture was poured into water and the steroid extracted into ethyl acetate. The organic solution was washed with sodium carbonate solution, then water, dried (MgSO₄) and the solvent evaporated to give a white froth. Preparative t.l.c. afforded the title compound (110 mg; 24%) as an analytically pure froth, having $v_{max}$ 3580 (hydroxyl), 1730 and 1250 (17-acetate), 1750 and 1210 (3-acetate), 1720 (20-ketone) and 1630 and 1280 cm$^{-1}$ (nitrate ester); $\lambda_{max}$ 267 nm ($\epsilon$500).

EXAMPLE 39

3-Acetoxy-19-norpregna-1,3,5(10)-trien-20-one

3-Hydroxy-19-norpregna-1,3,5(10)-trien-20-one (500 mg.) in pyridine (5 ml.) was treated with acetic anhydride (5 ml.) at ca. 90° for 2.5 hr. The solution was then evaporated in vacuo to dryness. The residue was filtered through magnesium silicate (1 g.) in methylene chloride, the solvent evaporated and the residual oil crystallized from cyclohexane to give the title compound (340 mg; 60%) m.p. 104°–105°, $[\alpha]_D$ + 141° (c. 0.69).

EXAMPLE 40

3-Acetoxy-9α,11β-dihydroxy-19-norpregna-1,3,5(10)-trien-20-one 11β-nitrate

A stirred solution of 3-acetoxy-19-norpregna-1,3,5(10)-trien-20-one (170 mg; 0.5 mmole) in acetic acid (5 ml.) was treated at room temperature with M aqueous ceric ammonium nitrate (2.3 ml; 1.15 equiv.) in one lot. After 20 min. the reaction mixture was poured into water (50 ml.) and the steroid extracted with ethyl acetate (50 ml.). The extract was washed with water (2 × 50 ml.) then evaporated. Preparative thin-layer chromatography of the residue (215 mg) afforded the title compound (69 mg; 33%) m.p. 165°–167° (dec.); $[\alpha]_D$ + 121° (c. 0.78).

EXAMPLE 41

3-Acetoxy-9α,11β-dihydroxy-oestra-1,3,5(10)-trien-17-one 11β-nitrate

Ceric sulphate dihydrate (10 g.) was stirred overnight with a solution of barium nitrate (13.5 g.) in N nitric acid (40 ml.) at room temperature and the resultant suspension centrifuged. The supernatant ca. 0.5M solution of ceric nitrate (8 ml.) was added to a stirred solution of 3-acetoxy-oestra-1,3,5(10)-trien-17-one (312 mg; 1 mmole) in acetic acid (10 ml.) at room temperature. After 30 min. the reaction mixture was poured into water, and the steroid was extracted into ethyl acetate. The extract was washed with water then with aqueous potassium hydrogen carbonate and the solvent was evaporated. Crystallisation of the residue from methanol gave the title compound (143 mg; 37%); m.p. 178°–181°, $[\alpha]_D$ + 108° (c. 0.50), contaminated with ca. 5% starting material.

EXAMPLE 42

3,17β-Diacetoxy-oestra-1,3,5(10)-triene-9α,11β-diol 11β-nitrate

A stirred solution of 3,17β-diacetoxy-oestra-1,3,5(10)-triene (356 mg.; 1 mmole) in acetic acid (10 ml.) was treated at room temperature with M aqueous ceric ammonium nitrate (4 ml). After 20 min., the solution was poured into water and the steroid was extracted into ethyl acetate. The extract was washed with water (twice) then aqueous potassium hydrogen carbonate, and the solvent was evaporated. Preparative thin-layer chromatography of the residue and crystallisation of the appropriate fraction from cyclohexane gave the title compound (157 mg; 35%), m.p. 173°–175° (slight dec.), $[\alpha]_D$ + 21° (c. 0.50).

EXAMPLE 43

3-Acetoxy-9α,11β-dihydroxy-1-methyl-19-norpregna-1,3,5(10)-trien-20-one 11β-nitrate 3-Acetoxy-1-methyl-19-norpregna-1,3,5(10)-trien-20-one (200 mg.) was dissolved in acetic acid (15 ml.) and ceric ammonium nitrate (1.3 g.) in 90% aqueous acetic acid (20 ml.) was added in one lot to the steroid solution. Aliquots of the reaction mixture were taken and the ceric ion content was estimated by titration with ferrous ammonium sulphate. After a reaction time of one hour at room temperature, no ceric ions remained and the reaction mixture was then poured into water (250 ml.). Diethyl ether was added and the steroid was extracted. The ether solution of the reaction product (250 ml.) was washed with 100 ml. lots of saturated sodium hydrogen carbonate solution until it was free of acetic acid and then with water until the washings were neutral. After washing the ether solution with saturated sodium chloride solution it was dried with anhydrous magnesium sulphate, filtered and evaporated to dryness in a rotary evaporator. The crude reaction product gave the following data:- t.l.c. showed a broad band and the reaction product did not crystallise. I.R. (in $CS_2$) 1635, 1280 and 860 (very strong intensity bands due to 11$\beta$-nitrate), 1760 (acetate) 1700 (C-20 carbonyl), 3500 cm.$^{-1}$ (9$\alpha$-OH).

n.m.r. 9.31 (small signal) (C-18 methyl or starting compound);

9.18 (strong signal C-18 methyl of title compound); 7.89 (C-21 methyl) 7.75 (3-acetate); 7.67 (1-methyl); 3.33 (2- and 4- hydrogens).

The crude yield of material was 190 m g. and the n.m.r. spectrum would suggest that 60–70% of this consisted of the title compound.

EXAMPLE 44

3-acetoxy-9$\alpha$,11$\beta$-dihydroxy-1-methyl-19-norpregna-1,3,5(10)-trien-20-one The hydroxy nitrate produced in Example 43 (200 mg.) was refluxed for 2 hours in 60 ml. of ethyl alcohol and 10 ml. of water together with 3 g. of zinc, after which time the zinc was filtered off, half the ethanol evaporated and the steroid product extracted with chloroform. The chloroform solution was washed with water before being dried ($MgSO_4$) and evaporated to yield the title compound (60–70% from acetone), m.p. 198°–200°, I.R. 3400 (broad band OH), 1760 (3-OAc), 1735, (17-C=O) n.m.r. 8.92, (C-18 methyl), 7.74 (3-OAc), 5.65 (triplet, J = 3 c.p.s. 11$\beta$-H), 3.10 and 2.68 (three aromatic H). T.L.C. $R_f$ = 0.65 with respect to oestrone acetate.

EXAMPLE 45

3-o-Nitrobenzoyloxy-9$\alpha$,11$\beta$-dihydroxyoestra-1,3,5(10)-trien-17-one 11$\beta$-nitrate 3-o-Nitrobenzoyloxyoestra-1,3,5(10)-trien-17-one (200 mg) in 90% aqueous acetic acid (70 ml) was reacted with ceric ammonium nitrate (1.05 g) for 24 hours. The product was isolated using the procedure discribed in Example 43. The title compound (25%) was obtained as crystals from ether, m.p. 150°–153°; NMR: $\tau$ 8.99 (C-18 methyl) and 4.14 (C-11$\alpha$ H); i.r. 1640, 1280, 860 and 3600 cm$^{-1}$.

EXAMPLE 46

3-Acetoxy-9$\alpha$,11$\beta$-dihydroxy-oestra-1,3,5(10)-trien-17-one 11$\beta$-nitrate 3-Acetoxy-9$\alpha$-hydroxyoestra-1,3,5(10)-trien-17-one (100 mg) was reacted with ceric ammonium nitrate (0.33 g) in 90% aqueous acetic acid (50 ml) for 1 hour. The mixture was poured into water and extracted with ether to yield title compound (30%) m.p. 188°–190° and also 3-acetoxyoestra-1,3,5(10),9(11)-tetraen-17-one (30%) arising from acid dehydration of the 9$\alpha$-hydroxy starting material and indicating that the starting material for the ceric oxidation is in fact the $\Delta^{9(11)}$ compound formed in situ.

EXAMPLE 47

3-Acetoxy-9$\beta$,11$\beta$-dihydroxy-oestra-1,3,5(10)-trien-17-one 11$\beta$-nitrate Oestrone acetate (3-acetoxyoestra-1,3,5(10)-trien-17-one) was oxidised as in Example 21. Preparative t.l.c. of the mother liquors after crystallisation yielded the 9$\beta$-isomer (ca 5%). I.R. bands at 3600, 1639, 1280 and 855 cm$^{-1}$; N.M.R. $\tau$ 8.89 (C-18 methyl) and 3.85 (11$\alpha$-H).

We claim:

1. A process for the preparation of a 9$\alpha$-hydroxy-11$\beta$-nitro-oxy steroid having an aromatic A-ring and carrying at the 1-, 4- and 13-positions H or $C_1$–$C_6$ alkyl; at the 3-position $C_1$–$C_6$ alkoxy; $C_1$–$C_6$ alkoxy substituted by phenyl or nitrophenyl; phenoxy; phenoxy substituted by nitro or methyl; sulphate nitrate, phosphate; or acyloxy selected from the group consisting of R.CO.O— where R is $C_1$–$C_6$ alkyl, $C_1$–$C_6$ alkyl substituted by phenyl or halo, phenyl or phenyl substituted by nitro or methyl and $R^1SO_2.O$— where $R^1$ is $C_1$–$C_6$ alkyl or phenyl or phenyl substituted by methyl; at the 16 position H, halo, methylene or $C_1$–$C_6$ alkyl; and at the 17-position keto or (a) H together with H, $C_1$–$C_8$ alkyl, $C_1$–$C_6$ alkyl substituted by at least one of keto, protected keto, hydroxy or acyloxy as defined for the 3-position, or (b) $C_1$–$C_6$ acyloxy as defined for the 3-position together with H, $C_1$–$C_8$ alkyl or $C_1$–$C_6$ alkyl substituted by at least one of keto, protected keto, hydroxy or acyloxy as defined for the 3-position, or (c) hydroxy together with H, $C_1$–$C_8$ alkyl or $C_1$–$C_6$ alkyl substituted by hydroxy or acyloxy as defined for the 3-position, which process comprises oxidising a corresponding 9,11-unsubstituted or 9,11-dehydro steroid with ceric ions in the presence of nitrate ions, provided that the A-ring of said 9,11-unsubstituted or 9,11-dehydro steroid does not carry an ether group together with a methyl group oxidisable under the reaction conditions.

2. A process as claimed in claim 1 in which the ceric ions are provided by ceric ammonium nitrate or ceric nitrate.

3. A process as claimed in claim 1 in which the reaction is effected in a water-miscible organic solvent.

4. A process as claimed in claim 3 in which the solvent contains a proportion of water.

5. A process as claimed in claim 3 in which the solvent is a mixture of at least one of dioxan and glacial acetic acid and water.

6. A process as claimed in claim 1 in which at least 4 molar equivalents of ceric salt are present initially.

7. The process as defined in claim 1 in which the 9,11-dehydro steroid is oxidized.

8. The process as claimed in claim 7 in which the 9,11-dehydro steroid is prepared by introducing a 9-hydroxy steroid corresponding to said 9,11-dehydro steroid into said ceric oxication system whereby said 9-hydroxy steroid is spontaneously dehydrated to form said 9,11-dehydro steroid.

9. A process as claimed in claim 1 in which any 9$\beta$-hydroxy-11$\beta$-nitro-oxy steroid also formed is isolated.

10. A compound of the formula

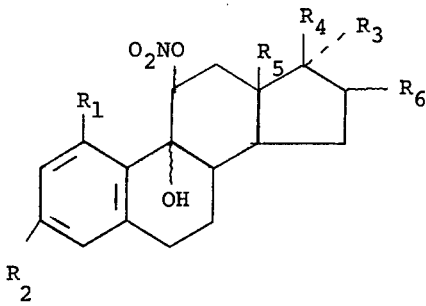

wherein $R_1$ is H or methyl;

$R_2$ is acyloxy selected from the group consisting of R.CO.O— where R is $C_1$–$C_6$ alkyl, $C_1$–$C_6$ alkyl substituted by phenyl or halo, phenyl or phenyl substituted by nitro or methyl; $R^1SO_2.O$— where $R^1$ is $C_1$–$C_6$ alkyl, phenyl or phenyl substituted by methyl; $C_1$–$C_6$ alkoxy; $C_1$–$C_6$ alkoxy substituted by phenyl or nitrophenyl; phenoxy; phenoxy substituted by nitro or methyl; sulphate; nitrate; or phosphate;

$R_3$ is hydrogen or acyloxy as defined hereinabove with respect to $R_2$ having from 1 to 6 carbon atoms;

$R_4$ is alkyl of up to 8 carbon atoms; hydroxy; R.CO.O— as defined hereinabove or $C_1$–$C_6$ alkyl substituted by at least one of keto, protected keto, hydroxy or $C_1$–$C_6$ acyloxy with the proviso that $R_3$ and $R_4$ shall not simultaneously be acyloxy; or $R_3$ and $R_4$ taken together are oxygen;

$R_5$ is H, methyl or ethyl; and $R_6$ is H, halo, methyl or methylene.

11. The compound of claim 10 wherein the 9-hydroxy substituent is a 9α-hydroxy group.

12. The compound of claim 10 wherein the 9-hydroxy substituent is a 9β-hydroxy group.

13. The compound as defined in claim 10 wherein $R_2$ is R.CO.O— where R is $C_1$–$C_6$ alkyl, $C_1$–$C_6$ alkyl substituted by phenyl or halo, phenyl or phenyl substituted by nitro or methyl; R $SO_2.O$— wherein $R^1$ is $C_1$–$C_6$ alkyl, phenyl or phenyl substituted by methyl; sulphate, nitrate; or phosphate.

14. The compound as defined in claim 13 wherein R is $C_1$–$C_6$ alkyl.

* * * * *